United States Patent
Hsieh et al.

(10) Patent No.: US 7,602,951 B2
(45) Date of Patent: Oct. 13, 2009

(54) METHOD AND SYSTEM FOR PROVIDING DEFECTIVE CELL CORRECTION IN A MEDICAL IMAGING DEVICE

(75) Inventors: Jiang Hsieh, Brookfield, WI (US); Paavana Sainath, Oconomowoc, WI (US); James Watkins Madine, Milwaukee, WI (US); Charles Hugh Shaughnessy, Milwaukee, WI (US); Eugene Clifford Williams, Waukesha, WI (US); Abdelaziz Ikhlef, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 968 days.

(21) Appl. No.: 11/079,355

(22) Filed: Mar. 14, 2005

(65) Prior Publication Data
US 2006/0204065 A1    Sep. 14, 2006

(51) Int. Cl.
*G06K 9/00*    (2006.01)
(52) U.S. Cl. ........................ 382/128; 382/131
(58) Field of Classification Search ............... 382/128, 382/131, 132, 149; 250/369
See application file for complete search history.

(56) References Cited

U.S. PATENT DOCUMENTS

| | | | | |
|---|---|---|---|---|
| 5,377,250 A | * | 12/1994 | Hu | 378/15 |
| 6,118,846 A | * | 9/2000 | Liu | 378/62 |
| 6,389,097 B1 | | 5/2002 | Bulkes et al. | |
| 7,034,873 B2 | * | 4/2006 | Mendis et al. | 348/246 |
| 2004/0222380 A1 | * | 11/2004 | Fuchs et al. | 250/369 |

OTHER PUBLICATIONS

D.-A. Sennst, M. Kachelriess, C. Leidecker, B. Schmidt, O. Watzke, and W. A. Kalender, An Extensible Software-based Platform for Reconstruction and Evaluation of CT Images, RadioGraphics 2004, p. 601-613, vol. 24.

* cited by examiner

*Primary Examiner*—Tom Y Lu
(74) *Attorney, Agent, or Firm*—Armstrong Teasdale LLP

(57) ABSTRACT

Methods and systems for scanning a patient by using a medical imaging device are provided. The methods include determining a defective cell in a row n of a detector of the medical imaging device, determining a mode of operation of the medical imaging device, estimating the output of the defective cell using the determined mode of operation and at least one of a conjugate sample of the defective cell, an adjusted conjugate sample of the defective cell, and an estimate of the output of the defective cell using an output of a corresponding cell in an adjacent row and reconstructing an image of the patient using the estimated value of the defective cell.

18 Claims, 14 Drawing Sheets

US 7,602,951 B2

METHOD AND SYSTEM FOR PROVIDING DEFECTIVE CELL CORRECTION IN A MEDICAL IMAGING DEVICE

BACKGROUND OF THE INVENTION

The invention relates generally to methods and system for reconstruction of computed tomography (CT) images, and more particularly to methods and system for correcting detector open cell errors.

In various known computed tomography (CT) imaging system configurations, an X-ray source in a CT scanner, projects a fan-shaped beam that passes through the object being imaged, such as a patient. The beam, after being attenuated by the object, impinges upon an array of radiation detectors. The intensity of the attenuated beam radiation received at the detector array is dependent upon the attenuation of the X-ray beam by the object. Each detector element of the array produces a separate electrical signal that is a measurement of the beam attenuation at the detector location. The attenuation measurements from all the detectors are used to reconstruct the image of the scanned object.

With the development of volumetric CT (VCT) scanner, the number of detectors in the scanner is increasing rapidly. Various known VCT scanners contain up to sixty four detector rows in which nearly 64000 detector cells are present for each detector. As a result, the probability of a detector channel failure increases.

Known techniques of dealing with a failed detector channel include replacement of the failed detector channel. However, replacement of failed detector channels leads to a significant increase in the cost of medical imaging systems and the downtime of the clinical operation of scanning a patient.

In addition, with the increasing number of detector channels contained in a CT scanner, it is not economical to replace all the failed detector channels. Various known techniques that determine and correct for failed detector channels are inadequate with some detector failure modes, such as detector open cell error. A detector open cell error occurs when a detector cell looses contact with the neighboring detector cells. The known techniques for image reconstruction produce images with severe artifacts caused due to some detector failure modes, such as detector open cell error.

BRIEF DESCRIPTION OF THE INVENTION

In an exemplary embodiment, a method of scanning a patient by using a medical imaging device is provided. The method includes determining a defective cell in a row n of a detector of the medical imaging device, determining a mode of operation of the medical imaging device, estimating the output of the defective cell using the determined mode of operation and at least one of a conjugate sample of the defective cell, an adjusted conjugate sample of the defective cell, and an estimate of the output of the defective cell using an output of a corresponding cell in an adjacent row, and reconstructing an image of the patient using the estimated value of the defective cell.

In another exemplary embodiment, a medical imaging system is provided. The medical imaging system includes a gantry at least partially circumscribing a patient viewing area and including at least one detector. The medical imaging system further includes a processor communicatively coupled to the detector. The processor is programmed to determine a defective cell in a detector of the medical imaging device and determine a mode of operation of the medical imaging device. The processor is further programmed to estimate the output of the defective cell using the determined mode of operation and at least one of a conjugate sample of the defective cell, an adjusted conjugate sample of the defective cell, and an estimate of the output of the defective cell using an output of a corresponding cell in an adjacent row and reconstruct an image of the patient by using the estimated value of the defective cell.

DETAILED DESCRIPTION OF THE INVENTION

Various embodiments of the invention provide a method and a system for scanning a patient by using a medical imaging device. The method includes identification of defective cells in a detector of the medical imaging device and providing correction for the identified defective cells, in order to obtain scanned images with reduced image artifacts.

Figure 1:
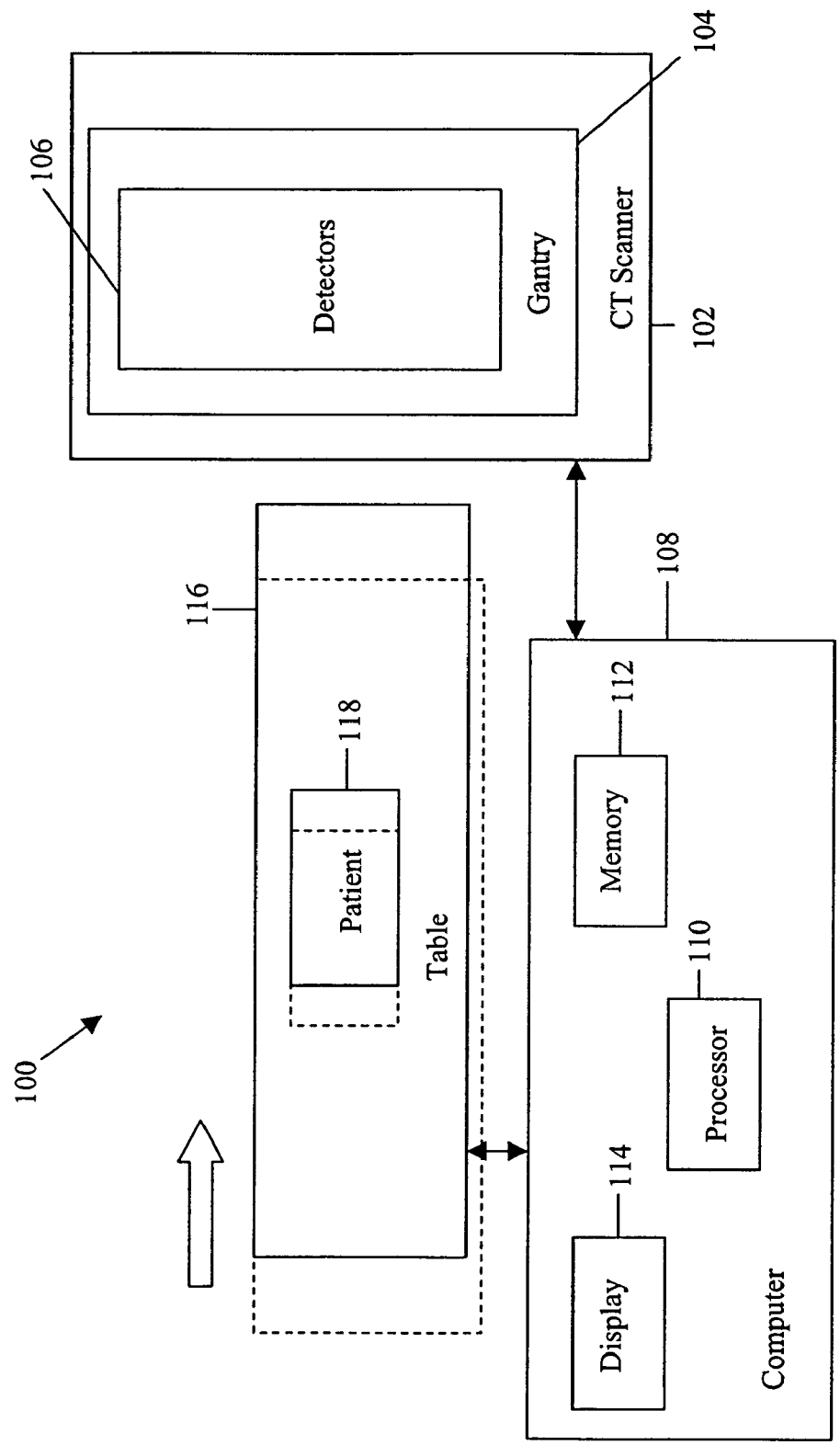
FIG. 1 is a block diagram illustrating a medical imaging system in accordance with an exemplary embodiment of the invention.

FIG. 1 is a block diagram illustrating a medical imaging system in accordance with an exemplary embodiment of the invention. Medical imaging device 100 includes a CT scanner 102, which includes a gantry 104. Gantry 104 contains detectors 106. Detectors 106, contain a plurality of detector cells arranged in a matrix. In an embodiment, each detector contains 6,40,000 detector cells. CT scanner 102 is coupled to a computer 108, which includes a processor 110, coupled to a memory unit 112 and a display unit 114. Processor 110 is communicatively coupled to detectors 106 through CT Scanner 102 and computer 108. Computer 108 is further coupled to a table 116 holding a patient 118. When CT scanner 102 operates in the step-and-shoot scan mode, gantry 104 moves around table 116 holding patient 118, enabling the patient's body to be scanned. However, when CT scanner 102 operates in the helical scan mode, table 116 holding patient 118 moves into gantry 104, in order to enable the patient's body to be scanned.

Figure 2:
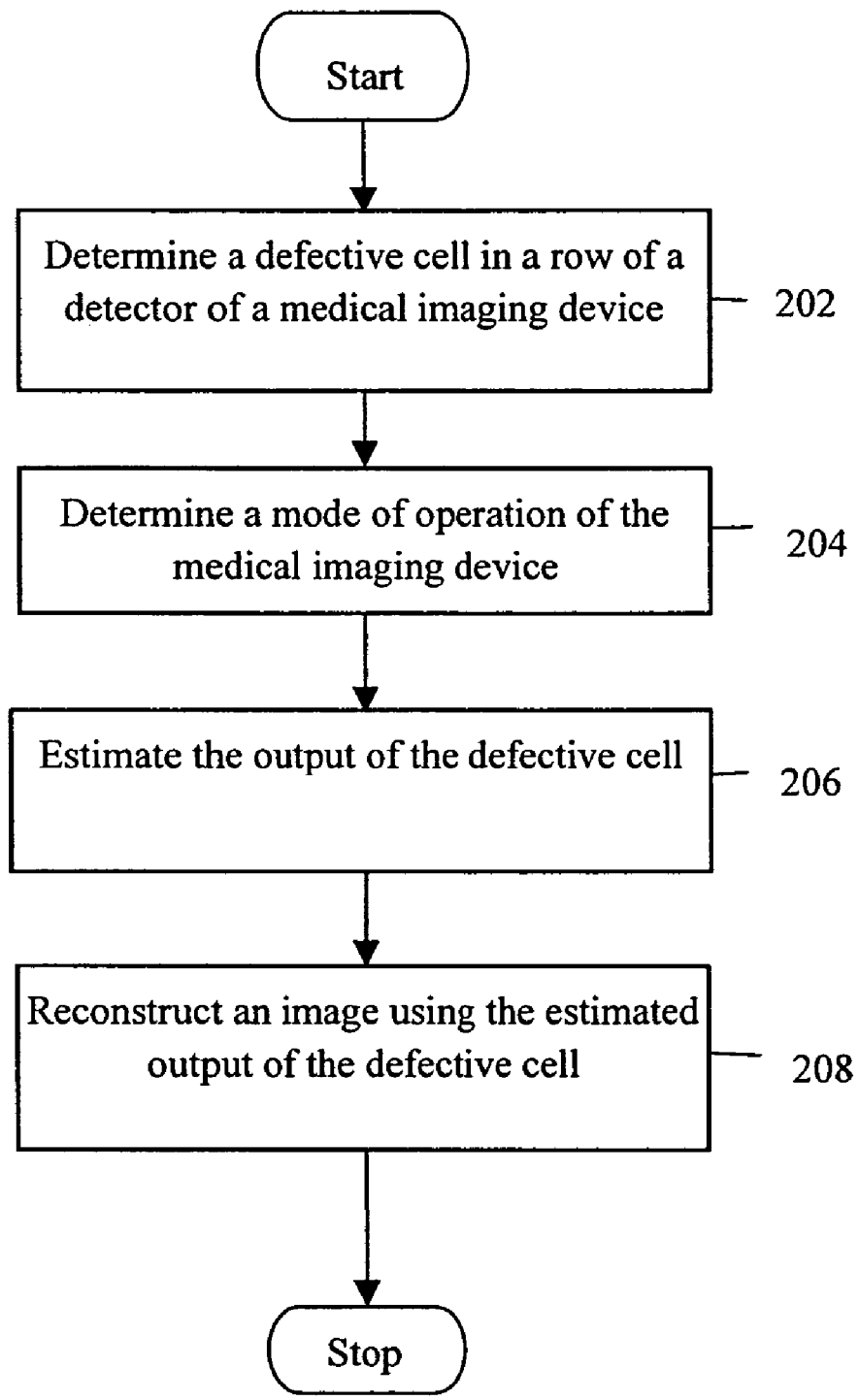
FIG. 2 is a flowchart illustrating a method of scanning a patient by using the medical imaging device in accordance with an exemplary embodiment of the invention.

FIG. 2 is a flowchart illustrating a method of scanning a patient by using medical imaging device 100 in accordance with an exemplary embodiment of the invention. At 202, a defective cell is determined in the detector cells of detectors 106. Determination of the defective cell includes determination of its position with respect to a row and a column of corresponding detector 106. In an embodiment of the invention, computer 108 is programmed to determine a defective cell in the detector cells of detectors 106.

At 204, mode of operation of medical imaging device 100 is determined. The mode of operation of medical imaging device 100 may be one of a step-and-shoot scan mode of operation with a fan beam projection, a step-and-shoot scan mode of operation with a conical beam projection, and a helical scan mode of operation. In an embodiment of the invention, computer 108 is programmed to determine mode of operation of medical imaging device 100.

AT 206, output of the defective cell is estimated using the determined mode of operation and at least one of a conjugate sample of the defective cell, an adjusted conjugate sample of the defective cell, and an estimate of the output of the defective cell using an output of a corresponding cell in a row adjacent to the row containing the defective cell. The estimation is made by using values from corresponding detector cells in a second row of detector cells that is adjacent to the first row of detector cells, respectively. In an embodiment of the invention, computer 108 is programmed to estimate output of the defective cell.

At 208, an image of patient 118 is reconstructed, by using the estimated value of the defective cell. This ensures that the defective cells do not produce image artifacts or significant degradation in the image quality of the reconstructed image. In an embodiment of the invention, computer 108 is programmed to reconstruct the image of the patient.

In various embodiments, tests such as those using offset noise, offset difference, linearity test and gain uniformity test are used to determine defective cells, such as open cells in detectors 106. These tests are used to develop a bad pixel map that is used to correct the reconstructed images. The bad pixel map enables the determination of defective cells in detectors 106. In an embodiment, the bad pixel map contains the position of each defective cell with respect to the various rows of detector cells. In another embodiment of the invention, computer 108 is programmed to determine the defective cells using at least one of offset noise, offset difference, linearity test and gain uniformity.

Figure 3:
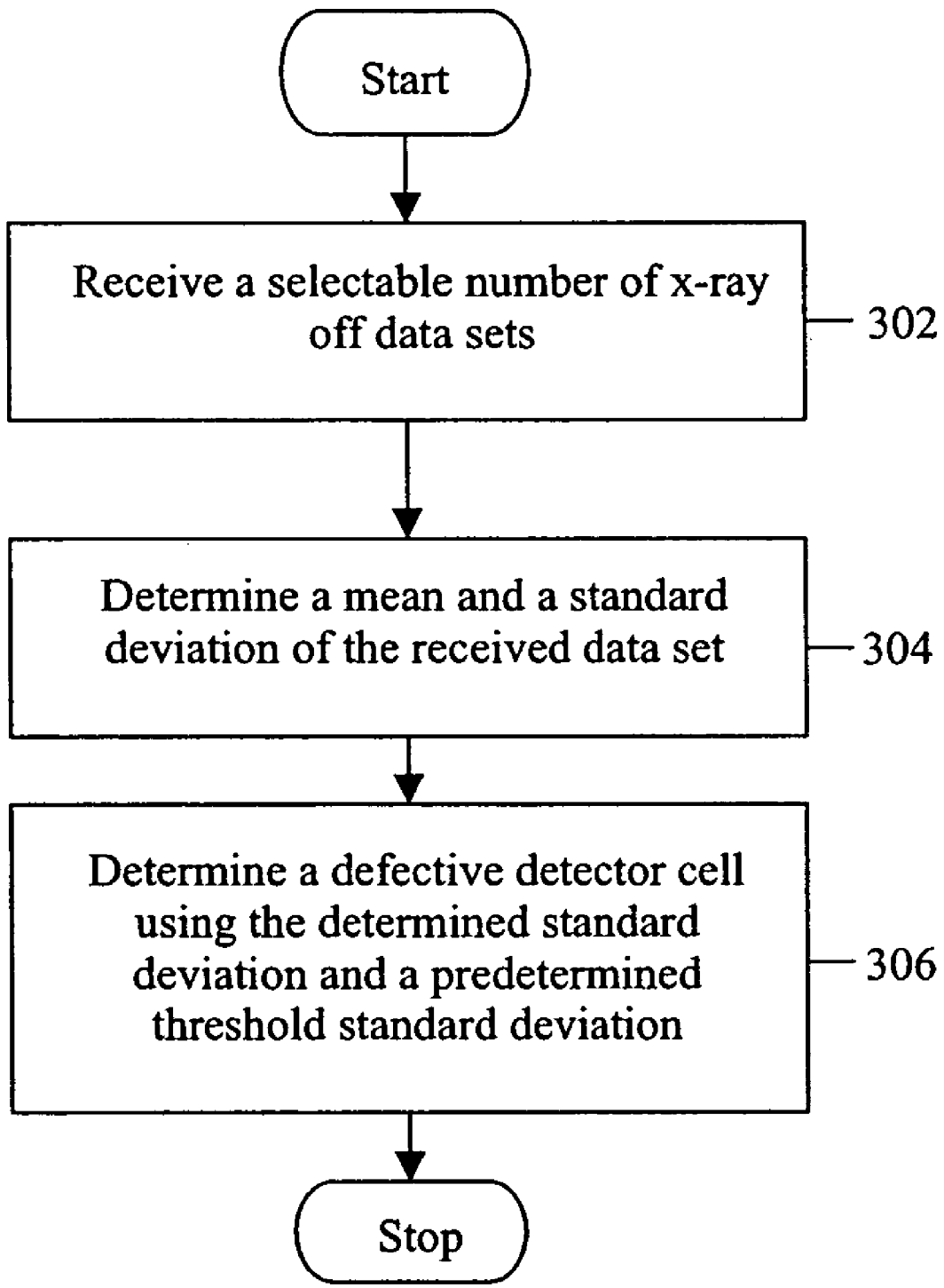
FIG. 3 is a flowchart illustrating a method for determining a defective cell in a detector by using offset noise in accordance with an exemplary embodiment of the invention.

FIG. 3 is a flowchart illustrating a method for determining a defective cell in detectors 106 by using offset noise in accordance with an exemplary embodiment of the invention. At 302, a selectable number of X-ray off data sets is obtained. The X-ray off data sets are obtained with the X-rays turned off, during an X-ray scan. Therefore, the X-ray off data sets correspond to electronic offsets. In various embodiments, around 500 to 1000 X-ray views are averaged to produce an X-ray off data set. At 304, a mean and a standard deviation of the obtained X-ray off data sets are determined for each pixel included in the data sets. The mean represents offset of each pixel in the X-ray off datasets.

At 306, a defective detector cell is determined by using the determined standard deviation and, a predetermined threshold standard deviation. In an embodiment, the pixels that have a standard deviation greater or less than a threshold value of 150 counts are included in the bad pixel map which, in turn leads to determination of defective cells.

In an embodiment, computer 108 is programmed to determine a defective cell in detectors 106.

Figure 4:
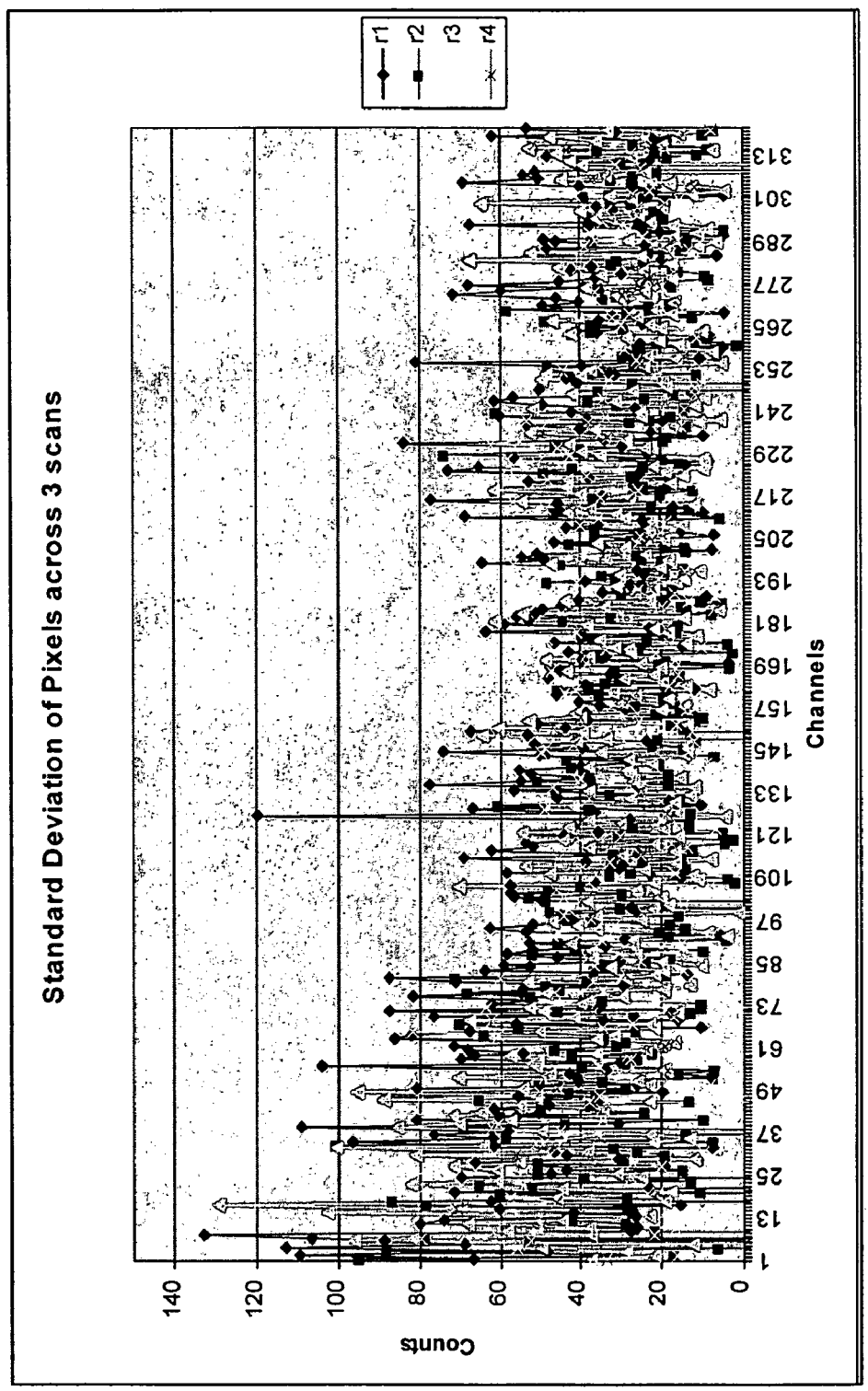
FIG. 4 illustrates a sample plot of pixel standard deviations across three offset scans.

FIG. 4 illustrates a sample plot of pixel standard deviations across three offset scans. The X-axis of the plot represents detector channels in medical imaging device 100 and the Y-axis represents the corresponding count. The plots labeled as 'r1', 'r2', 'r3', and 'r4' represent four different detector rows, from an exemplary 64 rows of detector cells.

Figure 5:
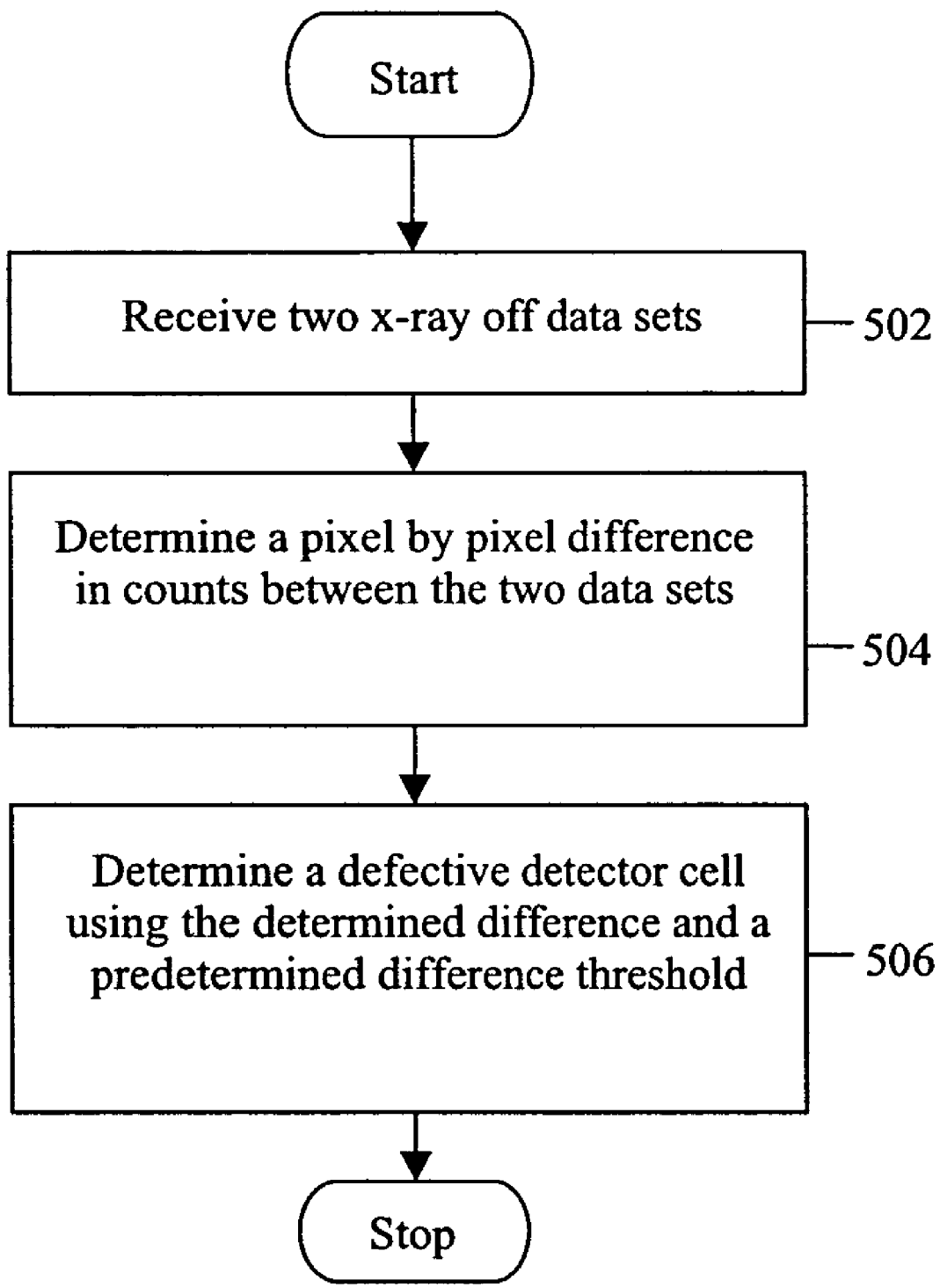
FIG. 5 is a flowchart illustrating a method for determining a defective cell in a detector by using offset difference in accordance with an exemplary embodiment of the invention.

FIG. 5 is a flowchart illustrating a method for determining a defective cell in a detector by using offset difference in accordance with an exemplary embodiment of the invention. At 502, two X-ray off data sets are obtained. At 504, a pixel-by-pixel difference in counts between the two data sets is obtained.

At 506, a defective detector cell is determined by using the determined difference between the two x-ray off data sets and, a predetermined difference threshold. In an embodiment, a median for all pixel by pixel differences is computed and, the pixels that are above 250 counts or below −250 counts are included in the bad pixel map which in turn leads to determination of defective cells.

In an embodiment, computer 108 is programmed to determine a defective cell in a detector by using offset difference.

Figure 6:
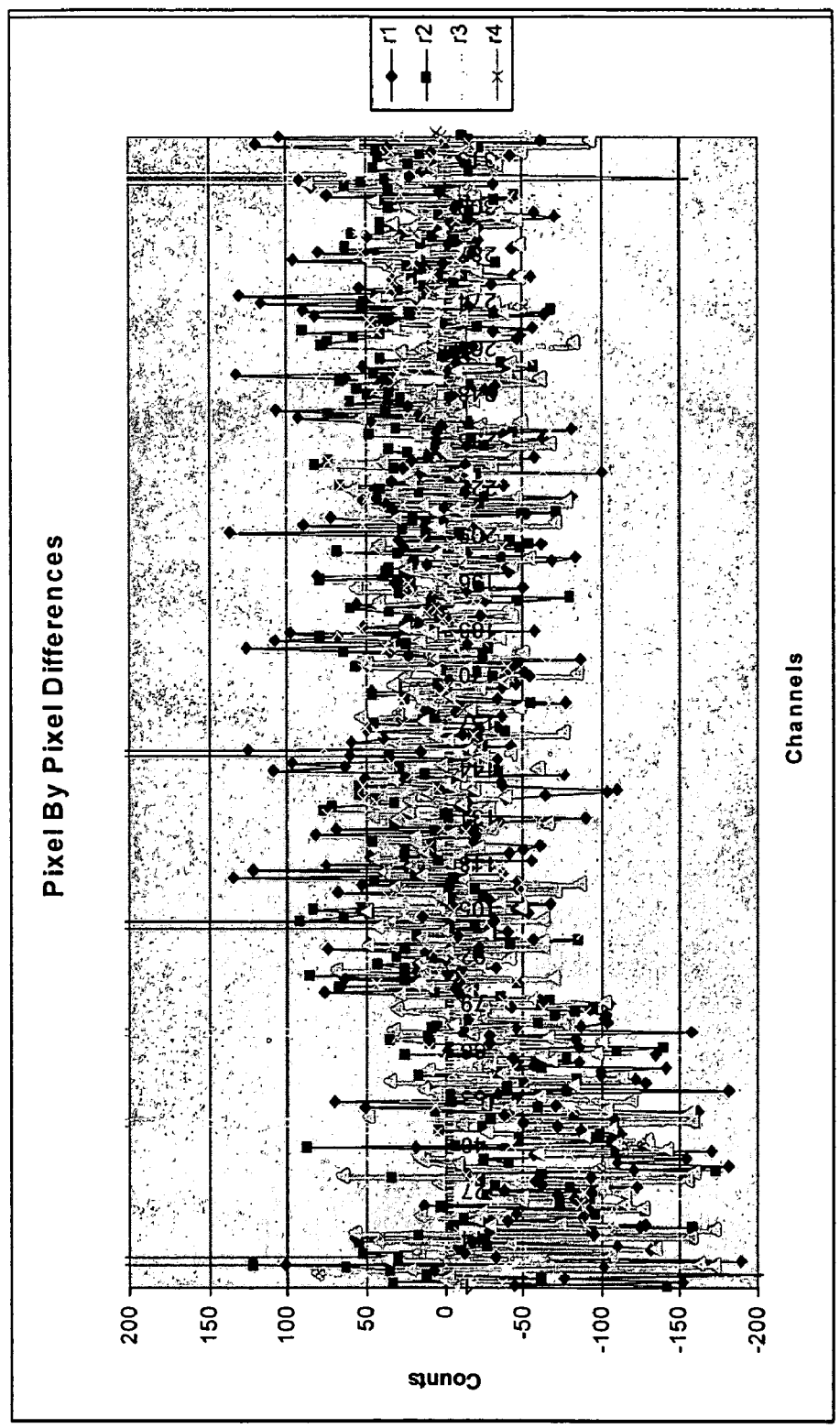
FIG. 6 illustrates a sample plot of the pixel-by-pixel differences of two offset scans in accordance with an exemplary embodiment of the invention.

FIG. 6 illustrates a sample plot of pixel-by-pixel differences of two offset scans. X-axis of the plot represents detector channels in medical imaging device 100 and Y-axis represents the corresponding count. The plots labeled as 'r1', 'r2', 'r3', and 'r4' represent four different detector rows, from an exemplary 64 rows of detector cells.

Figure 7:
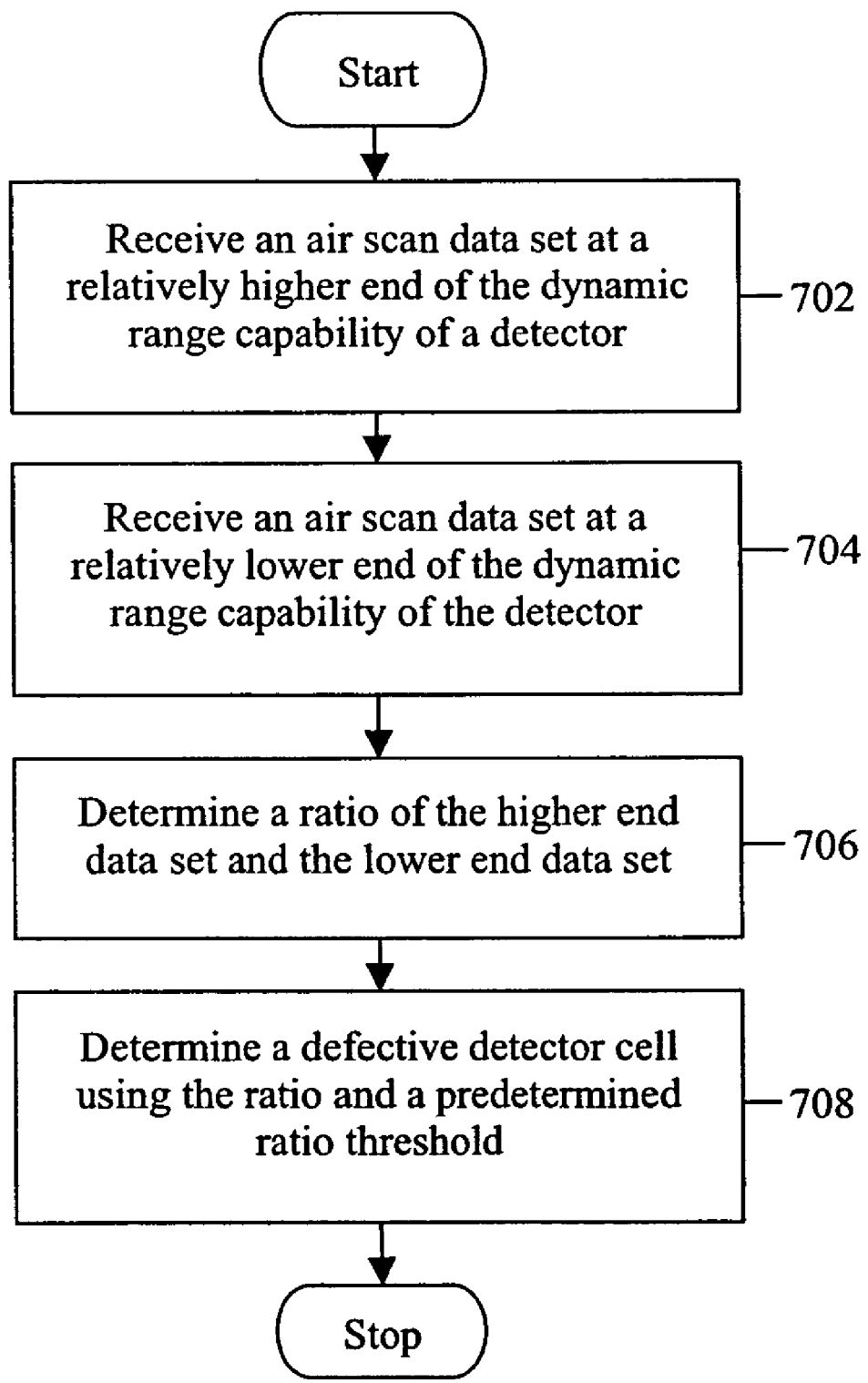
FIG. 7 is a flowchart illustrating a method for determining a defective cell in a detector by using linearity test in accordance with an exemplary embodiment of the invention.

FIG. 7 is a flowchart illustrating a method for determining a defective cell in a detector by using linearity test, in accordance with an exemplary embodiment of the invention. At 702, an air scan data set at a relatively high end of the dynamic range capability of the detector 106 is received. At 704, an air scan data set at a relatively low end of the dynamic range capability of the detector 105 is received. In various embodiments, the two air scans are obtained without bowtie filtration. In an embodiment, the two air scans are performed at two different tube current levels such as 600 mA and 50 mA.

At 706, a ratio of air scan data set at the higher end and air scan data set at the lower end is obtained. In various embodiments, the obtained air scan data is corrected for offset and normalized with respect to a reference before obtaining the ratio. In an embodiment, air scan data is corrected for offset by subtracting it from the collected offset data. In various embodiments, there are dedicated reference channels on one or both ends of the detector 106. These channels are designed so that they are exposed directly to X-rays, without patient blockage, during an X-ray scan being performed in clinical settings. The reading of the reference channels are averaged to produce a signal that is proportional to the X-ray tube flux. In an embodiment, the air scan data is normalized by dividing it by the reference signal on a view-by-view basis, to remove the effect of x-ray tube output fluctuation.

At 708, a defective detector cell, such as an open cell is determined by using the obtained ratio and, a predetermined ratio threshold. In an embodiment, the ratios, which are higher than 0.997 or lower than 1.003, are included in the bad pixel map, which, in turn leads to the determination of defective cells.

In an embodiment, computer 108 is programmed to determine a defective cell using linearity test.

Figure 8:
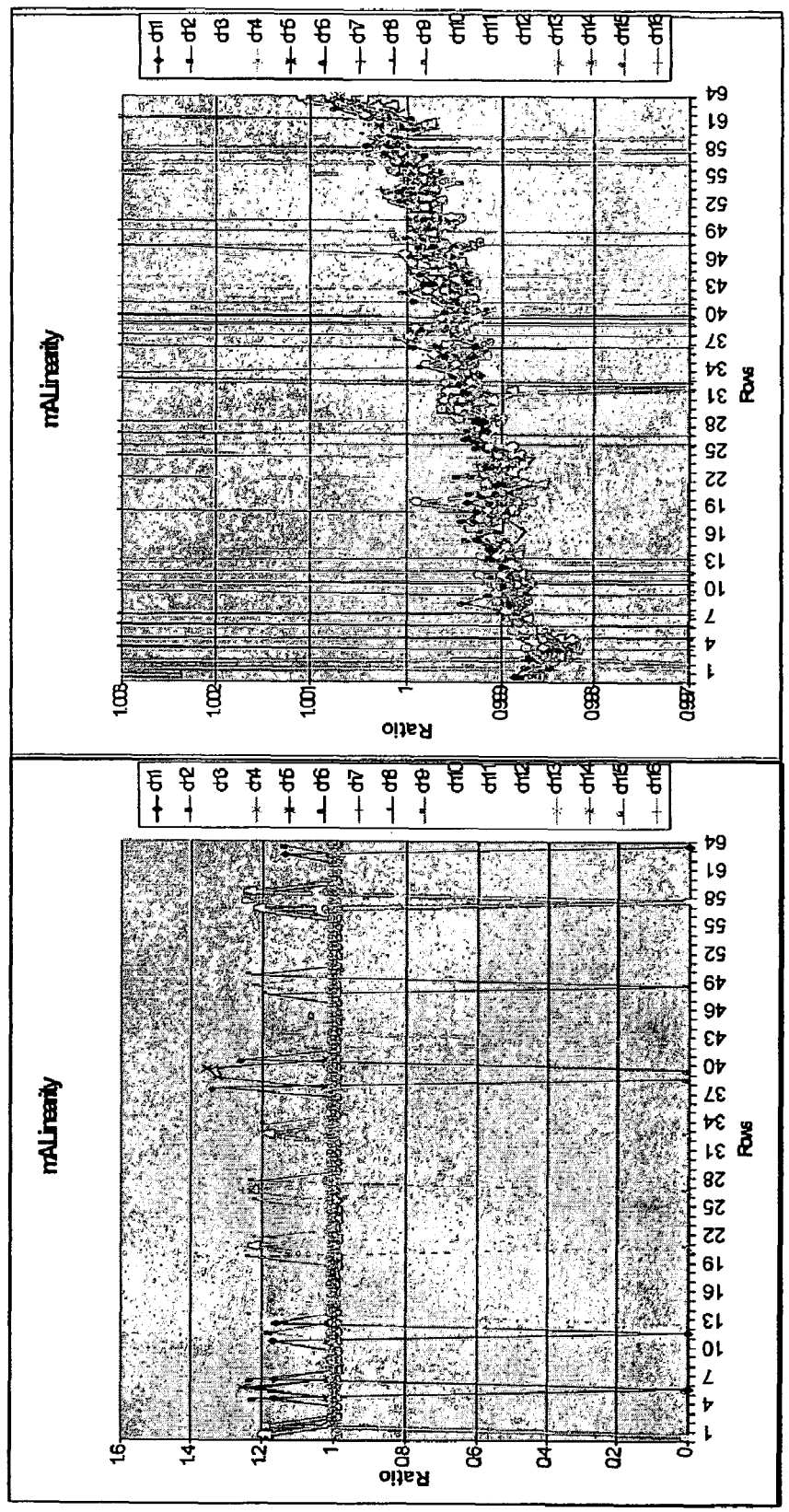
FIG. 8 illustrates sample plots of ratios of two scans taken at different mAs.

FIG. 8 illustrates sample plots of ratios of two scans taken at different mAs. The X-axis of the plot represents detector channels in medical imaging device 100 and the Y-axis represents the corresponding count.

Figure 9:
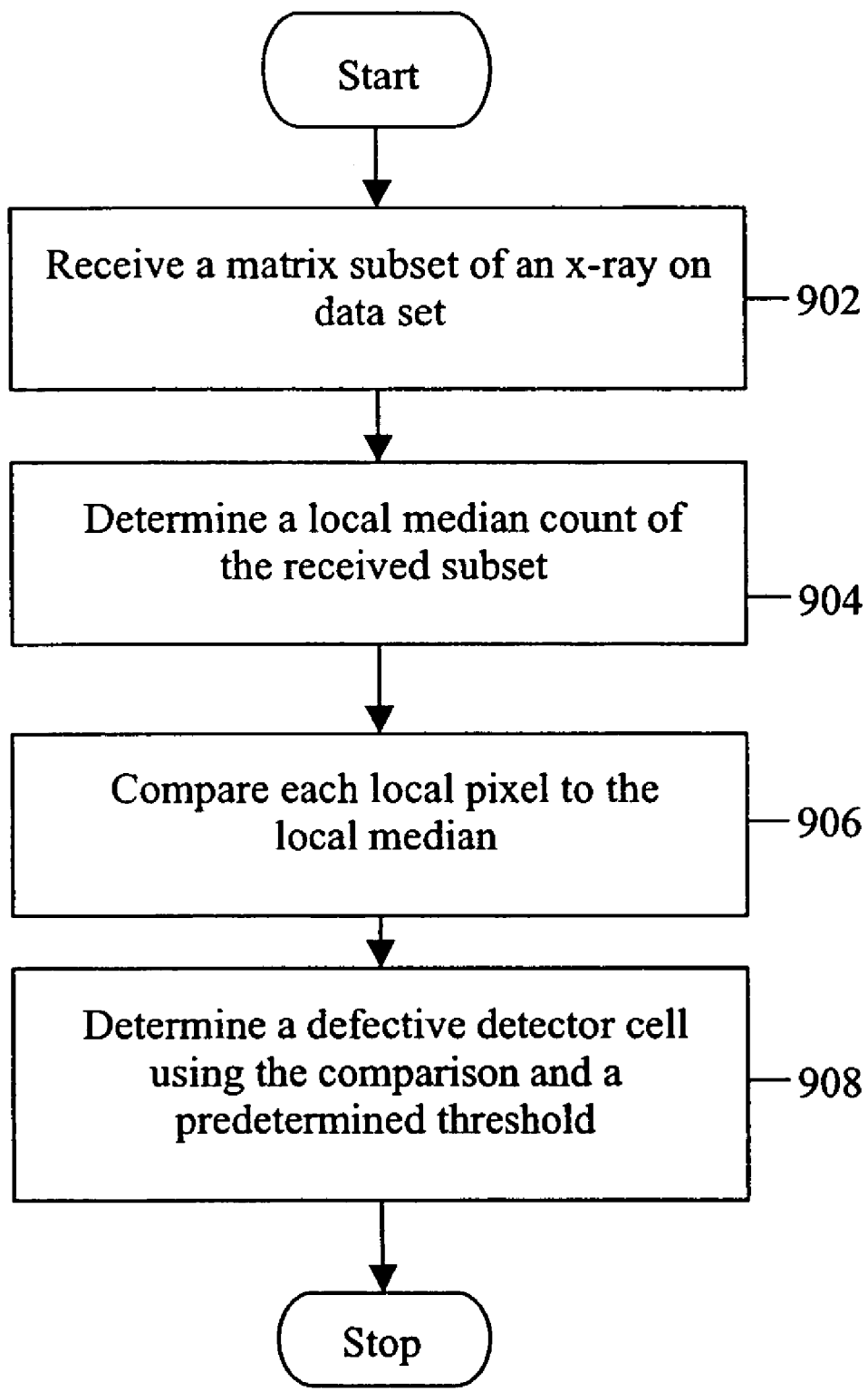
FIG. 9 is a flowchart illustrating a method for determining a defective cell in a detector by using gain uniformity in accordance with an exemplary embodiment of the invention.

FIG. 9 is a flowchart illustrating a method for determining a defective cell in a detector by using gain uniformity in accordance with an exemplary embodiment of the invention. At 902, a matrix subset of an X-ray on data set is received. In various embodiments, the received data set is corrected for offset, as described previously.

At 904, a local median count of the received X-ray on data set is determined. In various embodiments, the pixels that have already been included in the bad pixel map are not used for determining the local median count of the received X-ray on data set.

At 906, each pixel included in the received X-ray on data set is compared to the determined median. At 908, a defective detector cell is determined by using the result of the comparison and, a predetermined threshold. In an embodiment, the ratios that are higher or lower than a predetermined threshold are included in the bad pixel map, which, in turn leads to determination of defective cells. In an embodiment, if a pixel is less than 95% or more than 105% of the determined median, it is identified as a bad pixel and is included in the bad pixel map.

In an embodiment, computer 108 is programmed to determine a defective cell in detector 106 using gain uniformity.

Considering detectors 106, the charges collected at a defective cell, such as an open-cell or partially open-cell in a detector cannot be completely discharged through the detector. The charges that remain collected at the open cell affect the neighboring detector cells as well. Consequently, the projection samples of the open-cell, along with the projection samples of eight of its neighboring detector cells, when used for image construction, produce severe artifacts in the reconstructed image.

Figure 10:
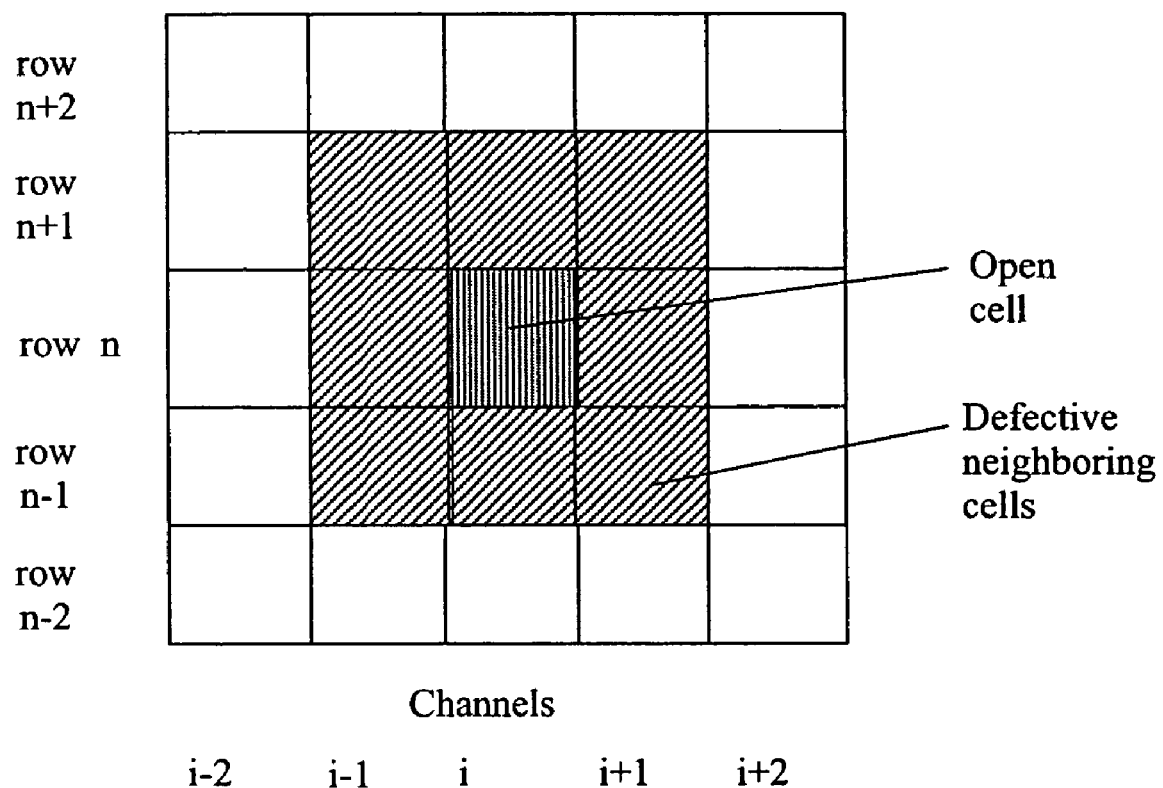
FIG. 10 illustrates an exemplary defective open cell along with eight affected neighboring cells.

FIG. 10 illustrates an exemplary defective cell, such as an open cell along with eight affected neighboring cells. It is assumed that the projection sample corresponding to detector row n and channel i is defective, being either open or partially open. The projection sample for this channel is denoted as $p_k(i,n)$, where k is the view index. This projection sample is defective and is not considered during image reconstruction. In various embodiments, the value of k ranges from a few hundreds to a few thousands. Therefore, the projection samples of the eight neighboring cells, $p_k(i', n')$, where $i-1 \leq i' \leq i+1, n-1 \leq n' \leq n+1$, are also defective. Various embodiments of the invention, estimate the projection samples for the eight neighboring cells $p_k(i', n')$ based on their neighboring cells.

In various embodiments, an image of a patient being scanned by medical imaging device 100 is reconstructed, by using an estimated value, such as a projection sample or a conjugate projection sample of the defective cell and its neighboring affected detector cells.

The projection samples collected with the volumetric CT detector include fan beam projection samples and cone beam projection samples. The fan beam projection samples and their conjugate projection samples are identical as they represent line integrals of the same X-ray path.

For fan beam projection samples collected by using step-and-shoot scan, two projection samples, $p(\gamma, \beta)$ and $p'(\gamma', \beta')$ are considered to be conjugate samples if they satisfy the following condition:

$$\begin{cases} \gamma' = -\gamma \\ \beta' = \beta + \pi + \gamma \end{cases} \quad (1)$$

For projection samples collected by using a volumetric CT scanner operating in the step-and-shoot mode, an additional detector row variable, n is used to define conjugate samples. Therefore, projection samples, $p(\gamma, \beta, n)$ and $p'(\gamma', \beta', n)$ are conjugate samples if equation (1) is satisfied.

In an embodiment, the missing values of the defective cell samples that are a part of fan beam projection samples are replaced with their conjugate samples. In another embodiment, computer 108 is programmed to replace the missing values of the defective cell with their conjugate samples. A final image of the scanned patient is reconstructed after performing the replacement, by using filtered backprojection technique.

In an embodiment, computer 108 is programmed to reconstruct images for fan beam projection samples collected by step-and-shoot scan.

Most of the projection samples collected by using a volumetric CT detector are not fan beam samples. Only the detector rows near the center plane of the detector lead to the collection of fan beam samples. The other parts of the detector lead to the collection of cone beam projection samples. The cone beam projection samples are not equal to their conjugate samples. Therefore, in various embodiments, additional adjustment is made in order to use the conjugate projection samples to estimate the defective cell missing projection.

In an embodiment, for a step-and-shoot cone beam scan, reconstruction of an image of the patient by using a conjugate projection sample of an defective cell includes, estimating an adjustment to the conjugate projection sample value by using a determined difference between the defective cell and the conjugate projection sample value. In another embodiment, computer 108 is programmed to estimate the adjustment to the conjugate projection sample value using the determined difference between the defective cell and the conjugate projection sample values.

Figure 11:
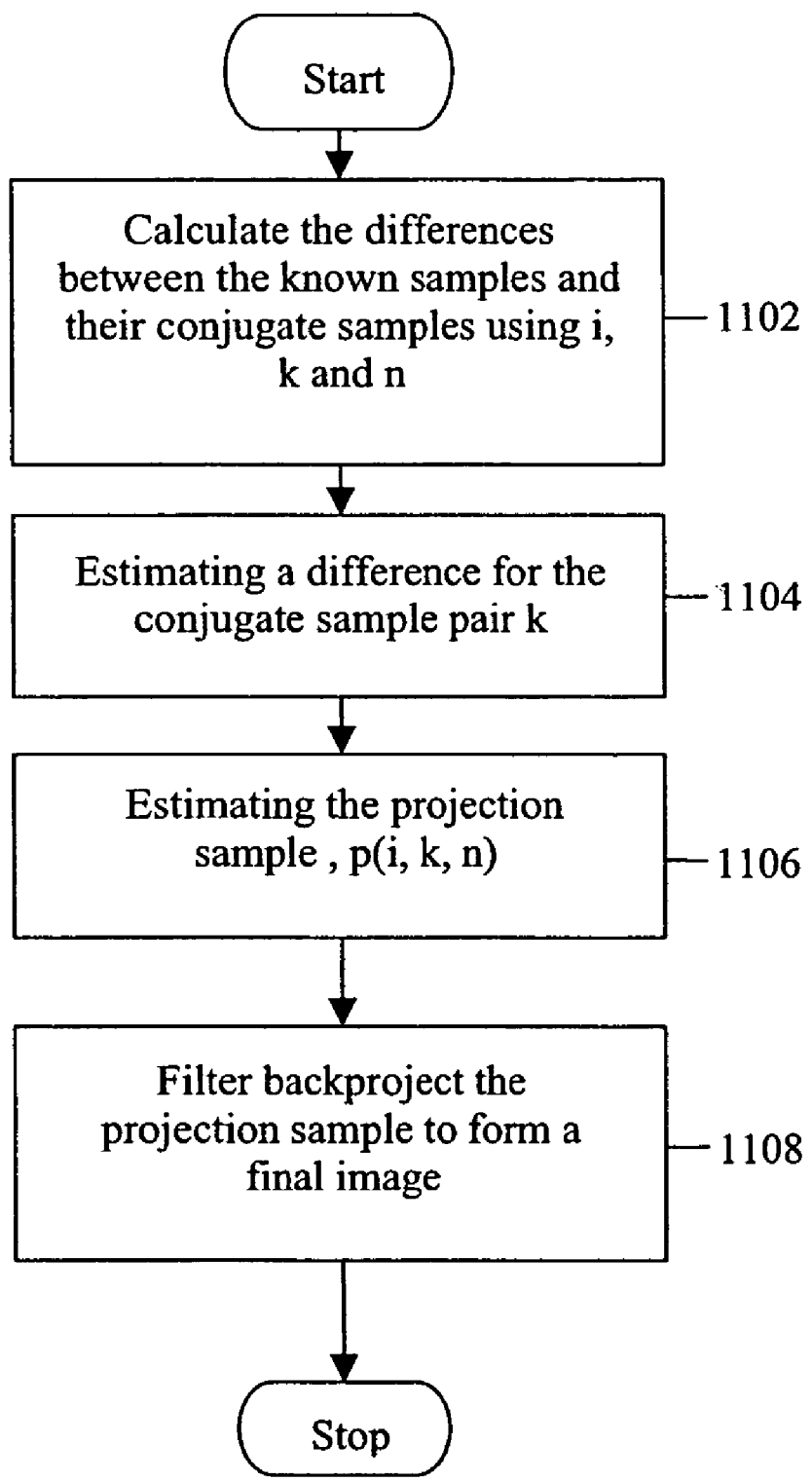
FIG. 11 is a flowchart illustrating a method for reconstructing an image of a patient for a step-and-shoot cone beam scan in accordance with an exemplary embodiment of the invention.

FIG. 11 is a flowchart illustrating a method for reconstructing an image of a patient for a step-and-shoot cone beam scan in accordance with an exemplary embodiment of the invention. $p'(i', k', n)$ denotes the conjugate sample for a step-and-shoot cone beam projection sample $p(i, k, n)$, where i denotes the detector channel index, k denotes the view index, and n denotes the detector row. i and k correspond to $\gamma$ and $\beta$ respectively as described in equation (1).

At 1102, the differences between the known cone beam projection samples and their conjugate samples, is calculated by using the following equations:

$$\Delta(i-2,k,n) = p'(i'-2,k',n) - p(i-2,k,n)$$

$$\Delta(i+2,k,n) = p'(i'+2,k',n) - p(i+2,k,n) \quad (2)$$

At 1104, a difference for the conjugate sample pair k is estimated. The estimated difference, $\Delta(i'')$, for the conjugate sample pair i'' is obtained by using the following equation:

$$\Delta(i'',k,n) = \Delta(i-2,k,n) + [\Delta(i+2,k,n) - \Delta(i-2,k,n)](i''-i+2)/4 \quad (3)$$

At 1106, the projection sample, $p(i, k, n)$, is estimated by using the following equation:

$$p(i,k,n) = p'(i',k',n) + \Delta(i'',k,n), \quad (4)$$

where $i-2 < i'' < i+2$

At 1108, filtered backprojection technique is applied to reconstruct the final scanned image after the projection sample, p(i, k, n), has been estimated.

In an embodiment, computer 108 is programmed to reconstruct an image of a patient for a step-and-shoot cone beam scan.

Figures 12A, 12B, 12C:
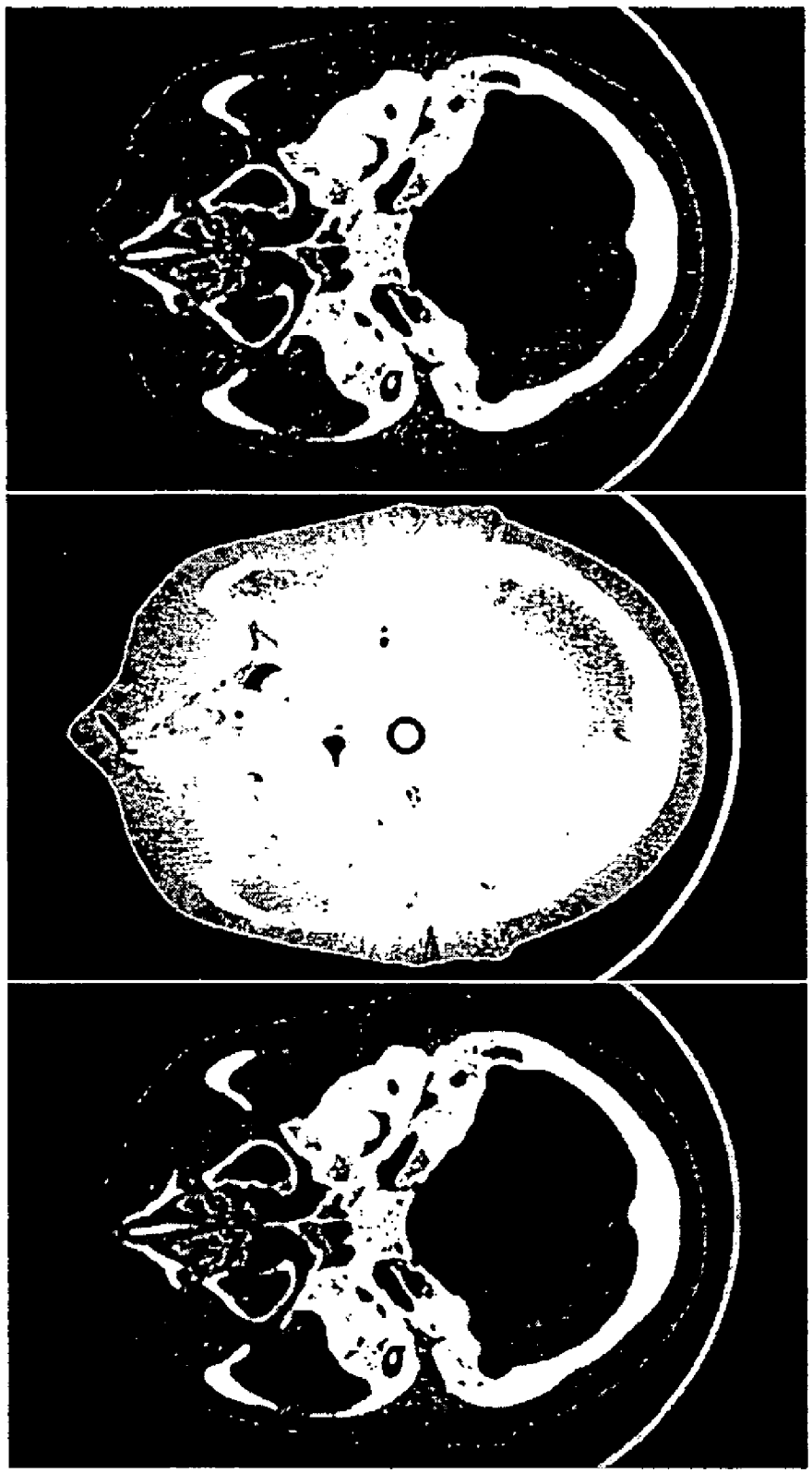
FIGS. 12A, 12B, and 12C illustrate reconstructed images of a human skull phantom, scanned by using step-and-shoot scan.

FIGS. 12A, 12B, and 12C illustrate reconstructed images of a human skull phantom scanned by using step-and-shoot scan. The scan illustrated in the figure is collected with a 16×0.625 mm detector configuration operating in a step-and-shoot mode. FIG. 12A illustrates the reconstructed image when there is no damaged detector cell. The projection samples for detector cells 436, 437, and 438 are set to zero for the detector rows 6, 7, and 8 in order to simulate a case, which includes defective cells, such as open-cells in the detector. The resulting scanned image is illustrated in FIG. 12B. The image presents severe artifacts due to the presence of the open cells in the detector. The correction algorithm described by using equations (2), (3) and (4) is then used to correct the created defective cells. The resultant image after performing the open cell correction is illustrated in FIG. 12C. The resultant image does not contain image artifacts and is identical to the original image illustrated in FIG. 12A.

Figure 13:
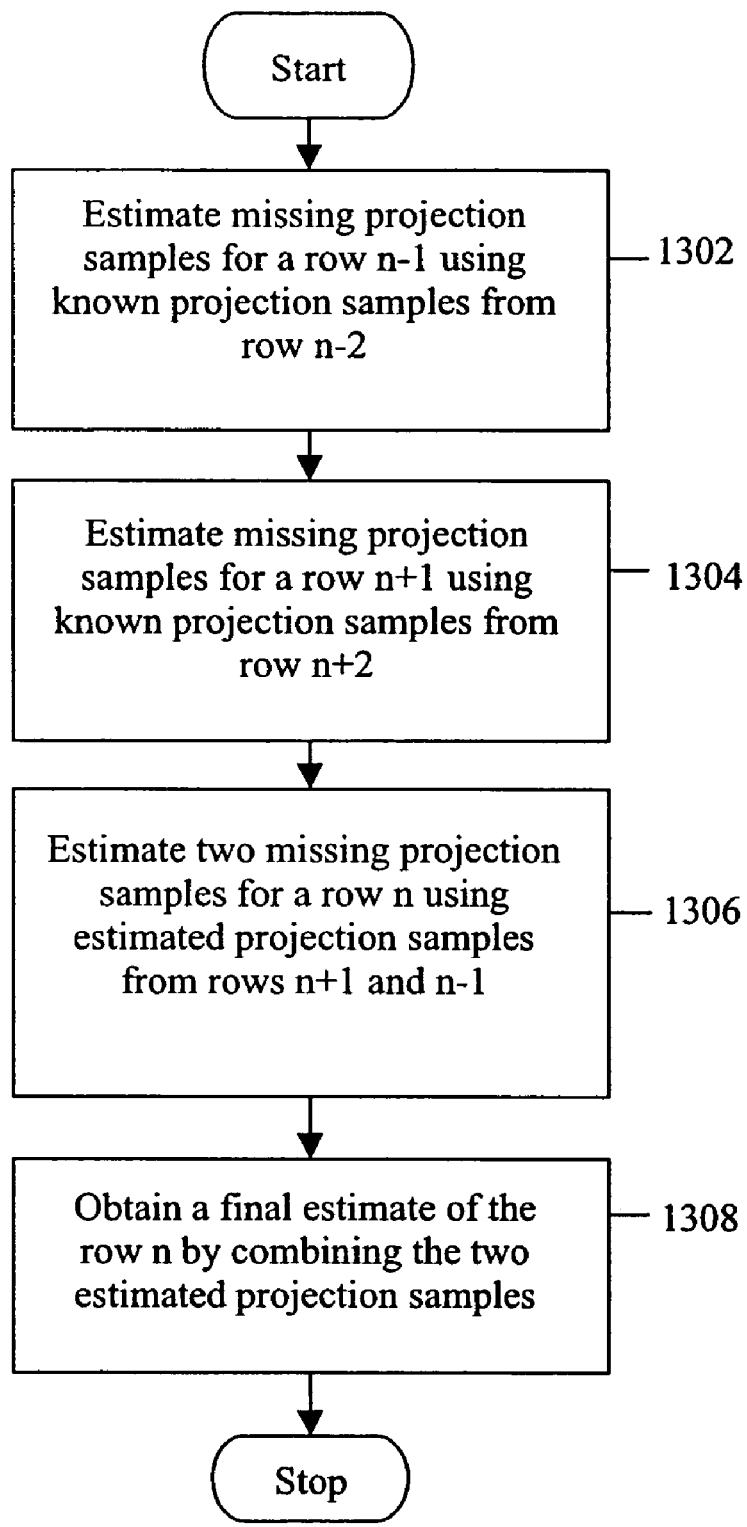
FIG. 13 is a flowchart illustrating a method for reconstructing an image of a patient for a helical cone beam scan in accordance with an exemplary embodiment of the invention.

FIG. 13 is a flowchart illustrating a method for reconstructing an image of a patient for a helical cone beam scan in accordance with an exemplary embodiment of the invention.

In an embodiment, the defective cell is assumed located at p(i, n). At 1302, missing projection samples for a row n−1 are estimated by using known projection samples from row n−2. This is achieved by firstly calculating the differences between rows n−1 and n−2 for the known projection samples by using the following equation:

$$\Delta_{n-2}(i-2) = p(i-2, n-1) - p(i-2, n-2)$$

$$\Delta_{n-2}(i+2) = p(i+2, n-1) - p(i+2, n-2) \quad (5)$$

Next an estimated difference of cell k between the two rows is calculated by using the following equation:

$$\Delta_{n-2}(j) = \Delta_{n-2}(i-2) + [\Delta_{n-2}(i+2) - \Delta_{n-2}(i-2)](j-i+2)/4, \ i-2 < i+2 \quad (6)$$

Finally, the estimated projection sample for the defective cell, p(j, n−1) in the row n−1, is obtained by using the following equation:

$$p(j, n-1) = p(j, n-2) + \Delta_{n-2}(j), \ i-2 < j < i+2 \quad (7)$$

The view index k used in equations (2), (3) and (4) is omitted for simplicity, since the algorithm described in equations (5), (6) and (7) is view independent. This is because the same calculation is being performed for every defective detector cell. In an embodiment, computer 108 is programmed to estimate missing projection samples for row n−1 using known projection samples from row n−2.

At 1304, missing projection samples for a row n+1 are estimated by using known projection samples from row n+2. The missing projection samples for the row n+1 are estimated by using equations (5), (6) and (7) by substituting (n+1) in place of (n−1) and (n+2) in place of (n−2) in the equations. In an embodiment, computer 108 is programmed to estimate missing projection samples for row n+1 using known projection samples from row n+2.

At 1306, two missing projection samples for a row n are estimated by using estimated projection samples from rows n+1 and n−1 respectively. Therefore, an estimation of projection sample of row n, p(j, n), is obtained from the estimated projection of row n−1, p(j, n−1) by using equations (5), (6) and (7) and replacing (n−1) by (n), and (n−2) by (n−1). In addition, an estimation of projection sample of row n, p″(k, n) is obtained from the estimated projection of row n+1 p(j, n+1) by using equations (5), (6) and (7) and replacing (n−1) by (n), and (n−2) by (n+1). In an embodiment, computer 108 is programmed to estimate missing projection samples for row n using estimated projection samples from rows n+1 and n−1.

At 1308, a final estimation for the sample projection of row n is obtained by combining the two estimated projections obtained at 1306. The final estimate is obtained by using the following equations:

$$w(j) = \frac{\Delta_{n-1}(j)}{\Delta_{n-1}(j) + \Delta_{n+1}(j)} \quad (8)$$

$$p(j, n) = [1 - w(j)]p(j, n) + w(j)p''(j, n) \quad (9)$$

where $\Delta_{n-1}(j)$ represents the quantity calculated in equation (6) for row n−1 and $\Delta_{n+1}(j)$ represents the same quantity for row n+1.

In an embodiment, the correction algorithm described by using equations (5), (6) and (7) is applied to high pitch helical scans. In various embodiments, the correction algorithm is applied to low pitch helical scans and, step and shoot scans as well. Helical pitch less than one is considered as low helical pitch and helical pitch greater than one is considered as high helical pitch.

In an embodiment, computer 108 is programmed to reconstruct an image of a patient for a helical cone beam scan.

Figures 14A, 14B, 14C:
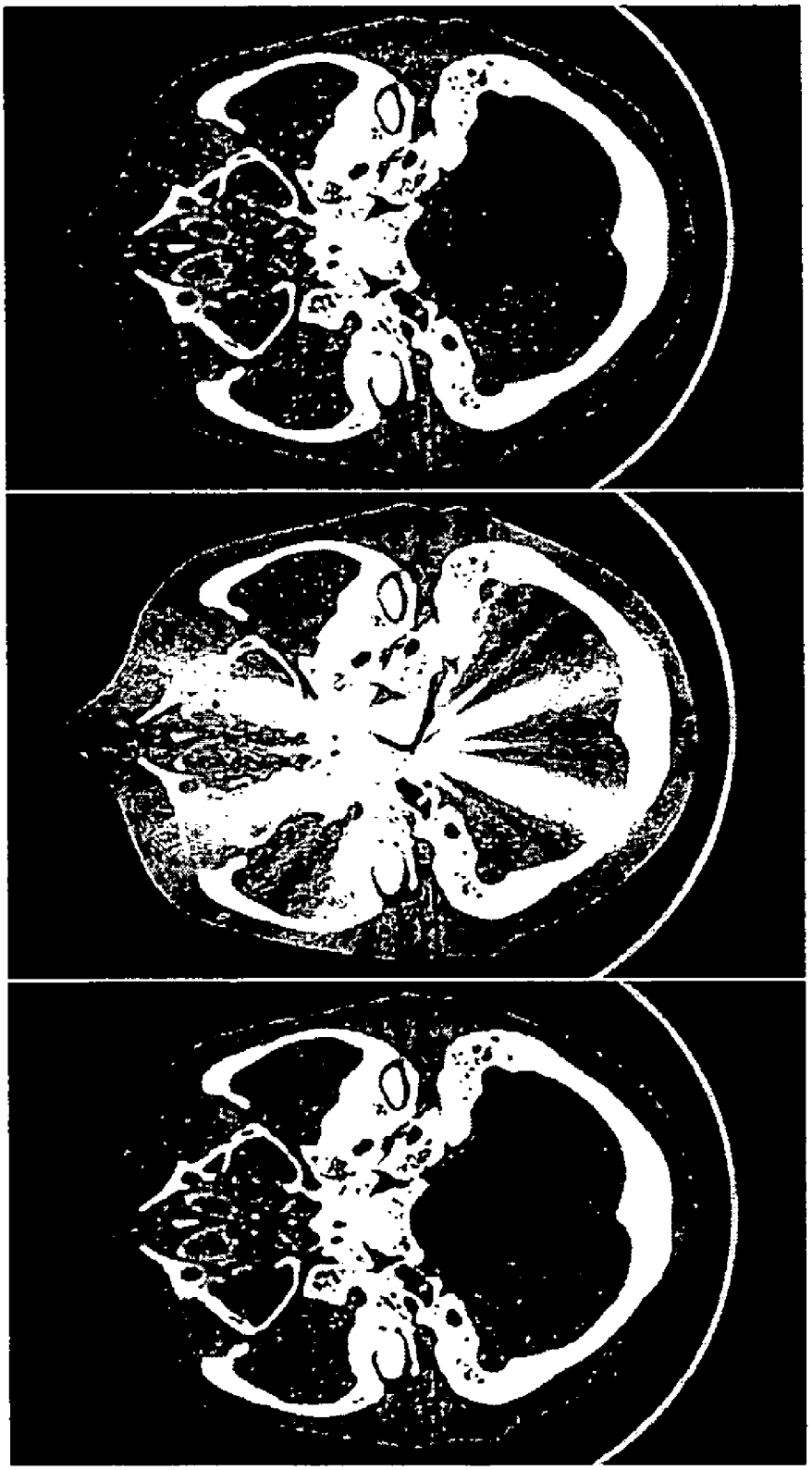
FIGS. 14A, 14B, and 14C illustrate reconstructed images of a human skull phantom, scanned by using helical scan.

FIGS. 14A, 14B, and 14C illustrate reconstructed images of a human skull phantom scanned by using helical scan. The scan illustrated in the figure is collected with a 16×0.625 mm detector configuration operating in a helical scan mode. FIG. 14A illustrates the reconstructed image when there is no damaged detector cell. The projection samples for detector cells 436, 437, and 438 are set to zero for the detector rows 6, 7, and 8 in order to simulate a case, which includes defective cells, such as open cells in the detector. The resulting scanned image is illustrated in FIG. 14B. The image presents severe artifacts due to the presence of the open cells in the detector. The correction algorithm described by using equations (5), (6), (7), (8) and (9) is then used to correct the created open-cells. The resultant image after performing the open cell correction is illustrated in FIG. 14C. The resultant image does not contain image artifacts and is identical to the original image illustrated in FIG. 14A.

The various embodiments of the invention provide an improved method of scanning a patient by using step-and-shoot and helical scans. Further, the various embodiments of the invention provide an improved method for identification of defective cells in a detector of a medical imaging device. The identification of defective cells enables providing correction for projection samples of the defective cells; in order to obtain scanned images with reduced image artifacts.

Further, various embodiments of the invention provide an improved method of reconstructing the scanned image of the patient by correcting the projection samples of a defective cell and its neighboring affected cells. The correction of defective cell projection samples provides better quality scanned images with reduced image artifacts.

A technical effect of the invention is to provide enhanced defective cell identification in a detector of a medical imaging device. Other technical effects include the reduction of image artifacts in a scanned image by providing correction for defective detector cells.

The various embodiments or components thereof may be implemented as part of a computer system. The computer system may include a computer, an input device, a display unit, and an interface, for example, for accessing the Internet. The computer may include a microprocessor. The microprocessor may be connected to a communication bus. The computer may also include a memory. The memory may include Random Access Memory (RAM) and Read Only Memory (ROM). The computer system further may include a storage device, which may be a hard disk drive or a removable storage drive such as a floppy disk drive, optical disk drive, and the like. The storage device can also be other similar means for loading computer programs or other instructions into the computer system.

As used herein, the term 'computer' may include any processor-based or microprocessor-based system including systems by using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term 'computer'.

The computer system executes a set of instructions that are stored in one or more storage elements, in order to process input data. The storage elements may also hold data or other information as desired or needed. The storage element may be in the form of an information source or a physical memory element within the processing machine.

The set of instructions may include various commands that instruct the processing machine to perform specific operations such as the processes of the various embodiments of the invention. The set of instructions may be in the form of a software program. The software may be in various forms such as system software or application software. Further, the software may be in the form of a collection of separate programs, a program module within a larger program or a portion of a program module. The software may also include modular programming in the form of object-oriented programming. The processing of input data by the processing machine may be in response to user commands, or in response to results of previous processing, or in response to a request made by another processing machine.

As used herein, the terms 'software' and 'firmware' are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

While the invention has been described in terms of various specific embodiments, those skilled in the art will recognize that the invention can be practiced with modification within the spirit and scope of the claims.

What is claimed is:

1. A method of scanning a patient using a medical imaging device, said method comprising:
    acquiring data sets using the medical imaging device, at least one data set representative of the patient;
    determining a defective cell in a row, n, of a detector of the medical imaging device using the acquired data sets;
    determining a mode of operation of the medical imaging device, the mode of operation being at least one of a step-and-shoot mode and a helical mode;
    estimating an output of the defective cell using the determined mode of operation and at least one of a conjugate sample of the defective cell, an adjusted conjugate sample of the defective cell, and an estimate of the output of the defective cell using an output of a corresponding cell in an adjacent row;
    reconstructing an image of the patient using the estimated output of the defective cell and the at least one data set representative of the patient; and
    outputting the reconstructed image.

2. A method in accordance with claim 1 wherein the mode of operation is at least one of a step and shoot mode of operation with a fan beam projection, a step and shoot mode of operation wit a conical beam projection and the defective cell proximate an axially center plane of the detector, and a helical scan mode of operation with a helical pitch less than one, and wherein reconstructing an image of the patient using the estimated value of the defective cell comprises replacing the value of the defective cell sample with a value of the conjugate projection sample of the defective cell.

3. A method in accordance with claim 1 wherein the mode of operation is a step and shoot mode of operation with a conical beam projection and the defective cell proximate an axial edge of the detector, wherein reconstructing an image of the patient using the estimated value of the defective cell comprises estimating an adjustment to the conjugate projection sample value using a determined difference between the defective cell and the conjugate projection sample value.

4. A method in accordance with claim 3 further comprising calculating a difference between respective known projection samples and their conjugate projection sample using:

$$\Delta(i-2,k,n)=p'(i'-2,k',n)-p(i-2,k,n), \text{ and}$$

$$\Delta(i+2,k,n)=p'(i'+2,k',n)-p(i+2,k,n), \text{ wherein}$$

p'(i'−2,k',n) is the conjugate projection sample for projection sample p(i−2,k,n),
where i is the detector channel index,
k is the view index, and
n is the detector row.

5. A method in accordance with claim 4 further comprising estimating a difference $\Delta(i'')$ for the conjugate sample pair i'' using:

$$\Delta(i'',k,n)=\Delta(i-2,k,n)+[\Delta(i+2,k,n)-\Delta(i-2,k,n)](i''-i+2)/4.$$

6. A method in accordance with claim 5 further comprising estimating the projection sample, p(i, k, n), using:

$$p(i,k,n)=p'(i',k',n)+\Delta(i'',k,n), \text{ for } i-2<i''<i+2.$$

7. A method in accordance with claim 6 further comprising filtered backprojecting the projection sample to form a final image.

8. A method in accordance with claim 1 wherein the mode of operation is a helical scan mode of operation with a helical pitch greater than one, and wherein reconstructing an image of the patient using the estimated value of the defective cell comprises:
    estimating missing projection samples for a row n−1 using known projection samples from row n−2;
    estimating missing projection samples for a row n−1 using known projection samples from row n−2; and
    estimating missing projection samples for a row n using estimated projection samples from rows n+1 and n−1.

9. A method in accordance with claim 8 wherein estimating missing projection samples for a row n using estimated projection samples from rows n+1 and n−1 comprises combining estimated projection samples from rows n+1 and n−1 using:

$$w(j) = \frac{\Delta_{n-1}(j)}{\Delta_{n-1}(j) + \Delta_{n+1}(j)}$$

$$p(j,n) = [1 - w(j)]p(j,n) + w(j)p''(j,n), \text{ where}$$

$\Delta_{n-1}(j)$ represents the quantity of an estimated difference of cell j from row n−1, $\Delta_{n+1}(j)$ represents the quantity of an estimated difference of cell j from row n+1.

10. A method in accordance with claim 8 wherein estimating missing projection samples for a row n−1 using known projection samples from row n−2 comprises determining a difference between a row n−1 and a row n−2 for the known samples using:

$$\Delta_{n-2}(i-2) = p(i-2,n-1) - p(i-2,n-2), \text{ and}$$

$$\Delta_{n-2}(i+2) = p(i+2,n-1) - p(i+2,n-2).$$

11. A method in accordance with claim 8 wherein estimating missing projection samples for a row n+1 using known projection samples from row n+2 comprises determining a difference between a row n+1 and a row n+2 for the known samples using:

$$\Delta_{n+2}(i-2) = p(i-2,n+1) - p(i-2,n+2) \text{ and}$$

$$\Delta_{n+2}(i+2) = p(i+2,n+1) - p(i+2,n+2).$$

12. A method in accordance with claim 8 wherein estimating missing projection samples for a row n comprises determining a difference between a row n+1 and a row n−1 for the known samples using:

$$\Delta_n(i-2) = p(i-2,n-1) - p(i-2,n+1), \text{ and}$$

$$\Delta_n(i+2) = p(i+2,n-1) - p(i+2,n-1).$$

13. A method in accordance with claim 8 further comprising filtered backprojecting the projection sample to form a final image.

14. A medical imaging system comprising:
a gantry at least partially circumscribing a patient viewing area, said gantry comprising at least one detector; and
a computer communicatively coupled to said detector, said computer programmed to:
determine a defective cell in a row, n, of said detector;
determine a mode of operation of said medical imaging device, the mode of operation being at least one of a step-and-shoot mode and a helical mode;
estimate an output of the defective cell using the determined mode of operation and at least one of a conjugate sample of the defective cell, an adjusted conjugate sample of the defective cell, and an estimate of the output of the defective cell using an output of a corresponding cell in an adjacent row; and
reconstruct an image of the patient using the estimated output of the defective cell.

15. A medical imaging system in accordance with claim 14 wherein said computer is further programmed to determine a defective cell in said detector using at least one of offset noise, offset difference, linearity test, and gain uniformity.

16. A medical imaging system in accordance with claim 14 wherein the mode of operation is at least one of a step and shoot mode of operation with a fan beam projection, a step and shoot mode of operation with a conical beam projection and the defective cell proximate an axially center plane of the detector, and a helical scan mode of operation with a helical pitch less than one, said computer is further programmed to replace the value of the defective cell projection sample with a value of a projection sample of a conjugate cell corresponding to the defective cell.

17. A medical imaging system in accordance with claim 14 wherein the mode of operation is a step and shoot mode of operation with a conical beam projection and the defective cell proximate an axial edge of the detector, said computer is further programmed to estimate an adjustment to the conjugate projection sample value using a determined difference between the defective cell and the conjugate projection sample value.

18. A medical imaging system in accordance with claim 14 wherein the mode of operation is a helical scan mode of operation with a helical pitch greater than one, said computer is further programmed to:
estimate missing projection samples for a row n−1 using known projection samples from row n−2;
estimate missing projection samples for a row n+1 using known projection samples from row n+2; and
estimate missing projection samples for a row n using estimated projection samples from rows n +1 and n−1.

\* \* \* \* \*

UNITED STATES PATENT AND TRADEMARK OFFICE
CERTIFICATE OF CORRECTION

PATENT NO.      : 7,602,951 B2                                      Page 1 of 1
APPLICATION NO. : 11/079355
DATED           : October 13, 2009
INVENTOR(S)     : Hsieh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1248 days.

Signed and Sealed this

Fifth Day of October, 2010

David J. Kappos
*Director of the United States Patent and Trademark Office*